United States Patent
Claus et al.

(10) Patent No.: US 9,971,870 B2
(45) Date of Patent: May 15, 2018

(54) SYSTEMS AND METHODS FOR MANAGING AND DISTRIBUTING USER PROFILES FOR SURGICAL SYSTEMS

(75) Inventors: Michael J. Claus, Newport Coast, CA (US); Joseph K. Liu, San Juan Capistrano, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 2350 days.

(21) Appl. No.: 11/839,074

(22) Filed: Aug. 15, 2007

(65) Prior Publication Data

US 2009/0049522 A1 Feb. 19, 2009

(51) Int. Cl.
*G06F 7/04* (2006.01)
*G06F 15/16* (2006.01)
*G06F 1/30* (2006.01)
*H04L 29/06* (2006.01)
*G06F 19/00* (2018.01)

(52) U.S. Cl.
CPC .............................. *G06F 19/3412* (2013.01)

(58) Field of Classification Search
USPC ........................................................ 705/2–3
See application file for complete search history.

(56) References Cited

U.S. PATENT DOCUMENTS

| 2004/0148403 | A1 | 7/2004 | Choubey et al. | |
|---|---|---|---|---|
| 2007/0255584 | A1* | 11/2007 | Pavlatos | G06F 19/322 705/2 |
| 2008/0319798 | A1* | 12/2008 | Kelley | G06F 19/323 705/3 |

FOREIGN PATENT DOCUMENTS

| WO | 96/13216 | 5/2006 |
|---|---|---|
| WO | 2007/016101 | 2/2007 |

* cited by examiner

*Primary Examiner* — Robert W Morgan
*Assistant Examiner* — Rajiv J Raj
(74) *Attorney, Agent, or Firm* — Johnson & Johnson Surgical Vision, Inc.

(57) ABSTRACT

A medical system is presented, where the system includes a medical profile directory configured to maintain a set of medical system profiles, a medical profile manager configured to update and maintain medical system profiles within the medical profile directory, and a server configured to interface with the medical profile manager to facilitate medical system profile maintenance. The server is configured to transmit information from at least one medical system profile to a surgical system, thereby enabling the surgical system to employ a current operational parameter within the medical system profile desired by a user.

12 Claims, 3 Drawing Sheets

SYSTEMS AND METHODS FOR MANAGING AND DISTRIBUTING USER PROFILES FOR SURGICAL SYSTEMS

FIELD OF THE INVENTION

The invention relates to systems and methods for medical care, and more particularly to systems and methods for managing and distributing user profiles within surgical systems.

BACKGROUND OF THE INVENTION

Surgical systems often require the configuration of a large and complex set of parameters and settings, typically specific settings requested or frequently employed by individuals such as surgeons. One medical system employing individual settings is a phacoemulsification system for ophthalmic surgery, used to remove the lens of an eye damaged by cataract. FIG. 1 shows a functional block diagram of a phacoemulsification system known in the art. The system 100 may include a control unit 102 and a handpiece 104 operably coupled together. As shown in FIG. 2, the handpiece 104 may include a needle 106 for insertion into an eye E and a vibrating unit 108 configured to ultrasonically vibrate the needle 106. The vibrating unit 108, which may include, e.g., a piezoelectric crystal, vibrates the needle 106 according to one or more parameters, such as frequency, pulse width, shape, size, duty cycle, amplitude, and so on.

It is common for each surgeon to use his or her own customized set(s) of parameters particular to the system, and it is not uncommon for surgeons to conduct surgical procedures at different locations. However, with current surgical systems, setting up a surgeon's customized set of parameters in every system the surgeon works with can be difficult, costly, and cumbersome. Accordingly, improved systems and methods for managing and distributing the surgeon's customized settings in multiple medical devices or systems such as phacoemulsification systems are desirable.

SUMMARY OF THE INVENTION

The invention is generally directed to systems and methods for medical care, and more particularly to systems and methods for managing and distributing user profiles for surgical systems.

According to one aspect of the present design, there is provided a medical system comprising a medical profile directory configured to maintain a set of medical system profiles, a medical profile manager configured to update and maintain medical system profiles within the medical profile directory, and a server configured to interface with the medical profile manager to facilitate medical system profile maintenance. The server is configured to transmit information from at least one medical system profile to a surgical system, thereby enabling the surgical system to employ a current operational parameter within the medical system profile desired by a user.

According to a second aspect of the present design, there is provided a method for providing medical system operating parameters to surgical systems. The method comprises collecting medical system operating parameters for at least one authorized user within at least one medical system profile, enabling the one medical system profile to be altered by at least one authorized user, and propagating the one medical system profile to at least one surgical system pursuant to predetermined propagation parameters.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
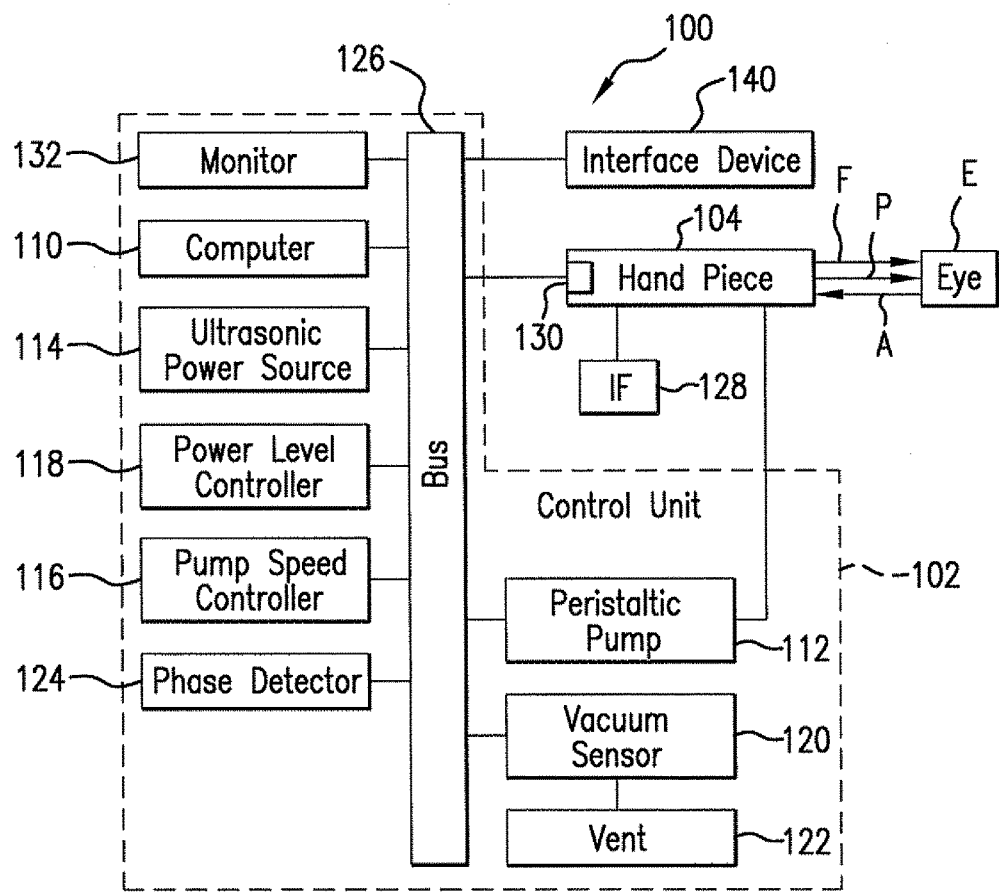
FIG. 1 shows a diagram of a phacoemulsification system known in the art.

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

While the present design may be used in various environments and applications, it will be discussed herein with a particular emphasis on a medical or hospital environment, where a surgeon or health care practitioner performs. For example, one embodiment of the present design is a phacoemulsification surgical system that comprises an independent graphical user interface (GUI) host module, an instrument host module, and a GUI device.

It is to be understood that any type of system having a large number of configuration parameter values to be set and centrally maintained may benefit from the design presented herein, and such a design is not limited to a phacoemulsification system or even a medical system. The present design may be implemented in, for example, systems including but not limited to phacoemulsification-vitrectomy systems, corneal correction systems, such as femtosecond and excimer laser systems, vitrectomy systems, dental systems, heart-lung surgical devices, industrial applications, communication network systems, access control systems, fire control/guidance devices, and aerospace applications.

The present design apparatus and method may employ various interface mechanisms to alter the database contents of the surgical instrument, such as via a GUI device, or other subsystem; it will be discussed herein with a particular emphasis on saving, recalling, and altering parameter values stored in the instruments database via a graphical user interface. The user interface device may include but is not limited to a touch screen monitor, mouse, keypad, foot pedal switch, and/or a computer monitor. The present design is intended to provide a basic user access or interface mechanism for viewing, altering, and managing a large number of configuration parameter values stored in a central database file system that affect the behavior of one or more remote surgical instruments.

The phacoemulsification system 100 typically includes a microprocessor computer 110 operably connected to and controlling various other elements of the system. In a number of embodiments, the system 100 may include a variable speed pump 112, such as a peristaltic and/or venturi pump, providing a vacuum source. The system may also include a pulsed ultrasonic power source 114 that provides control outputs to a pump speed controller 116 and an ultrasonic power level controller 118. A vacuum sensor 120 provides an input to the computer 110 representing the vacuum level on the output side of the pump 112. Venting may be provided by a vent 122. The system 100 may also include a phase detector 124 for providing an input to the computer 100 that represents a phase shift between a sine wave representation of the voltage applied to the handpiece 104 and the resultant current into the handpiece 104. The functional representation of the system 100 also includes a system bus 126 to enable the various elements to be operably in communication with each other.

In operation, the control unit 102 supplies ultrasonic power to the phacoemulsification handpiece 104. An irrigation fluid source 128 provides irrigation fluid to the handpiece 104. The irrigation fluid and an ultrasonic pulse are applied by the handpiece 104 to a patient's eye E, which are indicated by arrows F and P, respectively. Aspiration of the eye E is achieved by means of the pump 112, which is indicated by arrow A. The handpiece 104 may include a switch 130 for enabling a surgeon to select an amplitude of electrical pulses to the handpiece 104 via the computer 110, the power level controller 118, and the ultrasonic power source 114. The operation of the system 100 in general may be in accordance with the disclosure of U.S. Pat. No. 6,629,948, which is incorporated herein in its entirety by reference.

As shown above, there are many parameters of the system 100 that can be set by the surgeon associated with the various functions described above, e.g., type of ultrasonic power level (such as continuous, pulsed, t-phaco, or combinations there), max rate of aspiration, max rate of irrigation, and other parameters and modes of operation, such as those disclosed in U.S. patent application Ser. No. 11/401,529 entitled "Application of a system parameter as a method and mechanism for controlling eye chamber stability," which is hereby incorporated by reference in its entirety. These parameters can be controllable by various interfaces, such as computer user interfaces and/or foot pedals/switches. An example computer user interface for system 100 is described in U.S. patent application Ser. No. 11/030,443 entitled "Phacoemulsification System Utilizing Graphical User Interfaces for Adjusting Pulse Parameters," and an example foot pedal/switch control is described in U.S. Pat. No. 4,983,901 entitled "Digital Electronic Foot Control for Medical Apparatus and the Like" and U.S. Pat. No. 5,268,624 entitled "Footpedal Control with User Selectable Operational Ranges." All three of these references are hereby incorporated by reference in their entirety into the present application.

Figure 2:
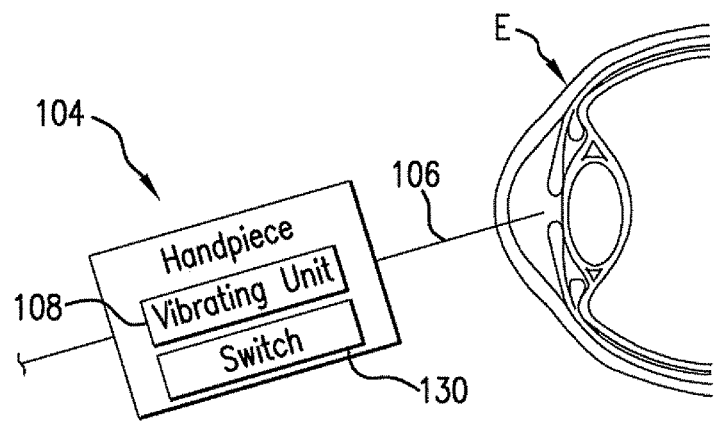
FIG. 2 illustrates a handpiece for a phacoemulsification system known in the art.

FIG. 2 illustrates the general components of handpiece 104 and its interaction with eye E. Handpiece 104 includes vibrating unit 108 and switch 130, which typically enables the surgeon to switch between vibrating states, such as going from a "chop" state to a "sculpt" state, wherein the ultrasonic energy from the handpiece 104 varies. Needle 106 vibrates and contacts eye E pursuant to vibrations received from vibrating unit 108.

The present design enables the surgeon to enter his or her desired settings for the medical device, a phacoemulsification system in this embodiment. A series of settings can be employed by a surgeon, such as a max pulse amplitude, pulse shape, footpedal settings, max aspiration rate, max irrigation rate, and other settings desired by the surgeon, such as those described above. In the past, the surgeon might have to manually enter the setting or have the settings input for her before commencing surgery, a time consuming and costly procedure. The present design maintains a surgeon's desired settings at a central location and allows those settings to be distributed or used on multiple phaco or medical machines. In this manner, a change by the surgeon can pass to the central location and propagate through the system or network and be available on other similar machines. Furthermore, these settings can be easily shared by other surgeons at remote locations.

Figure 3:
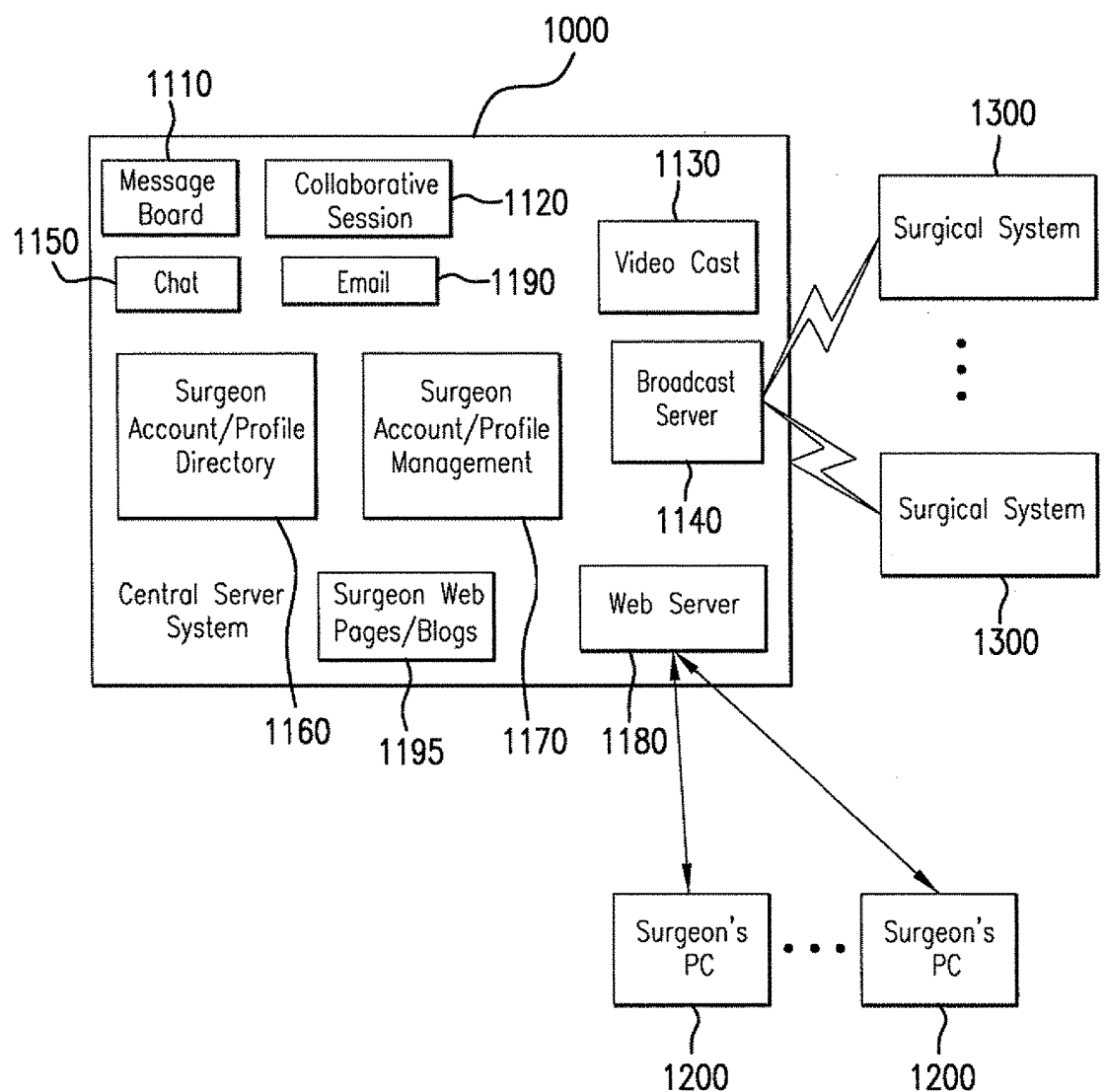
FIG. 3 is a medical system in accordance with the teachings provided herein.

FIG. 3 illustrates a central server system 1000 for managing and distributing surgeon user settings for a surgical system 1300, such as a phacoemulsification system 100 or a corneal correction system such as an excimer and/or femtosecond laser (not shown). The surgical system 1300 includes a set of parameters for configuration, e.g., in the case of a phacoemulsification system 100, such as those described above. These parameters can be stored as a surgeon's customizeable profile in a data file. The data files for the various surgeons can be stored in a central surgeon account database or directory 1160 within the central server system 1000. A typical profile may include settable parameters and that individual's desired settings, if provided, or a set or at least one default setting. For example, if a surgeon does not wish to employ a specific aspiration setting but has specific power setting requirements, a default aspiration parameter or set of parameters may be provided in her profile. The profile may be in any desired form, including but not limited to a database file, text file, or other electronic file or electronic information repository known in the art. In this description, the information pertinent to the medical device in question and associated with the surgeon or individual will be called a profile, but it is to be specifically understood that the term profile refers to any general collection of information pertinent to execution of the functionality described herein and generally associated with an individual.

The central server 1000 may support various modules or functions which may link various computing devices or electronic devices, including but not limited to email 1190, chat 1150, video cast 1130, message boards 1110, and surgeon web pages or blogs 195. Multiple components or servers or devices or software may be employed to effectuate the functionality provided in central server system 1000.

Surgeon account or profile manager 1170 may interact with web server 1180 and central surgeon account database or directory 1160 to manage multiple surgeon profiles. In general, three pertinent functions may be performed by Surgeon account or profile manager 1170 and central surgeon account database or directory 1160: receiving or initially obtaining a profile, altering a profile, and propagating a profile. Regarding initially obtaining a profile, if surgeon X's profile has not been provided, it may be received at web server 1180, either from a surgeon's PC 1200 or from a surgical system 1300 via broadcast server 1140, The profile for surgeon X may be received and surgeon account or profile manager 1170 may provide surgeon X's profile to central surgeon account database or directory 1160 for the express purpose of maintaining the profile. Altering or updating a profile may be accomplished by the surgeon or other person acting through the surgeon's PC 1200 or surgical system 1300 to update a particular entry in the file or even the entire profile. Note that while the PCs here are labeled surgeon PCs 1200, they may in fact be any authorized data entry device, including a wireless device, wired device, PC, phone, PDA, or any other device enabling a user to receive and edit his or her profile once authorized. If the surgeon wishes to change his profile, he may request his profile, which may be available locally or may be obtained via web server or server 1180 and surgeon account or profile manager or medical profile manager 1170 from surgeon account database or directory 1160, also known as a medical profile directory. The surgeon may then alter his profile at his client device or PC, for example changing his desired pulse amplitude settings, and save his profile. Changes to the profile may be provided to web server 1180 and subsequently to surgeon account or profile manager 1170 which updates the profile in surgeon account database or directory 1160. The surgeon can make changes to his profile at a client device or at a surgical system 1300. The result is an updated profile for the particular surgeon or user maintained in surgeon account database or directory 1160.

The surgeon may also elect to share or publish his/her profile to other surgeons to enable discussion, collaboration, and optimization of profiles. With this collaboration, a surgeon can adopt a profile from another surgeon, such as a key opinion leader, and simply update his/her surgical system 1300 accordingly.

A new or updated profile can be distributed to all systems in the field. Two general ways of updating profiles may be employed—either when updates are made, propagating throughout the system, or periodic propagation such as sending the profiles out at low usage times for the network. A combination of these may be provided. The propagation of updates when received can provide ready access to updated information, but monitoring profile changes and propagating at irregular times can be costly in terms of processing and network traffic. Periodic updating can control processing and network traffic costs, but can result in old profiles being maintained on surgical systems 1300.

Propagation through the system may be initiated from the central server system or from outside the central server system 1000, such as by an administrator or administrator device issuing a "propogate" type of command to the central server system 1000. Such a command may be generated by surgeon account or profile manager 1170 or within surgeon account database or directory 1160 itself. Once a propagate type command is issued, or the time for propagation passes via a counter counting down or similar method, the surgeon account or profile manager 1170 may retrieve any or all of the profiles in surgeon account database or directory 1160 and direct them to web server 1180 for propagation to desired devices, including but not limited to surgical systems 1300. If desired, a certain propagation map can be generated, such as propagate all profiles to all devices, including surgeon PCs 1300, once per week, and to surgical systems once per day, and for surgeons residing or practicing in country X or state X or hospital system X, propagate profiles to surgical systems in country X or state X or hospital system X every two hours. Other predetermined arrangements for propagating can be provided. During propagation, web server 1180 may receive profiles and provide the profiles to broadcast server 1140, which broadcasts the profiles to surgical system 1300.

Propagation may occur for all profiles, certain selected or predetermined profiles, profiles that have been updated since the last propagation, or in some other desired manner. Propagation may take place wirelessly or over a wired transmission system or combination of both. Broadcast server 1130 may transmit information and receive information over the air or wirelessly.

An alternative updating method is for the user to log onto a surgical system 1300 and to either request a profile update or have the surgical system 1300 automatically request an updated profile from central server system 1000. In this arrangement, surgical system 1300 may maintain a set of profiles locally or may not maintain any profiles locally. If no profiles are maintained locally, the surgical system must obtain profiles from central server system 1000 whenever appropriate, such as when a surgeon logs into or uses the system. Alternately, for example, in a situation where four surgeons are expected to use one specific surgical system 1300 at a particular site, the surgical system 1300 may obtain the current profiles for those four surgeons from central server system 1000 via web server 1180, surgeon account or profile manager 1170, and surgeon account database or directory 1160. The surgical system may obtain one or more profiles in this manner at any appropriate time, may obtain each user's profile at a given time, or a combination of both. In this manner, specific profiles may be obtained when desired.

Regarding specific component functionality, the components illustrated in FIG. 3 may be combined or may be split among various devices while still performing the functionality desired. For example, the surgeon account or profile manager 1170 may be combined with the surgeon account database or directory 1160 on a single device, such as an ASIC or semiconductor having memory, and web server 1180 may comprise more than one device, which generally includes computing hardware, such as those from IBM, Hewlett Packard, or Dell, and access management, network and database software known in the art, such as those from Microsoft, Oracle, Siebel, SAP, and others. In general, the surgeon account or profile manager 1170 is a device or software that exhibits the functionality of maintaining profiles, typically indexed such that they can be updated and efficiently passed to other devices in the system when desired, such as a software database residing in memory. Surgeon account database or directory 1160 is a device or software that exhibits the functionality of seeking profiles from surgeon account or profile manager 1170 when requested, receiving requests or commands from web server 1180 and/or broadcast server 1140 and providing information and/or profiles to those devices or elements, and performing other functions, including but not limited to reporting that particular profiles are unavailable if an errant request is received, assigning tags or indexes to profiles, and so forth.

Web server 1180 is typically a device that receives data from and transmits data to client devices, such as the surgeon's PCs 1200 shown in FIG. 3. Other client devices or intermediate devices, such as wireless devices or routers or nodes may be employed. Further, while not specifically shown in FIG. 3, web server 1180 may transmit information to surgical systems 1300 if desired. In essence, web server 1180 controls all information transmitted from and received by central server system 1100, including propagation requests, profile requests, and so forth, and directs the information to and from the appropriate component or components. One skilled in the art would be able to employ a typical web server device and configure the device to perform the functionality described herein. Web server 1180 may interface with or be formed with broadcast server 1140, which again is either hardware or software having the functionality of interfacing with the surgical systems 1300 deployed in the field. Broadcast server may therefore receive information from or transmit information to web server 1180 and/or surgeon account or profile manager 1170 for the purpose of receiving profiles or profile updates or providing profiles or profile updates to surgical systems 1300.

Many operating rooms do not have computer networking capability. In other words, the rooms do not have physical network connections to enable surgical systems to be networked with other computing devices outside of the room; however, adding such networking equipment may be undesirable, because it could require cables and other hardware that could impede the mobility of the surgical systems (which are often on wheels to give the surgeon the flexibility to move systems around for optimum spacing). One approach is to use a wireless network, i.e., a network that allows these computing systems to communicate with each other and remote systems wirelessly, e.g., a wireless LAN or personal area network (PAN). An implementation of a wireless network is to include a wireless network component in each system (e.g., a wireless network card, network adapter, or PAN compatible device, such as a Bluetooth, IrDA, UWB, or the like compatible device) configured to communicate with a local or nearby wireless router, e.g., an 802.11 router known in the art, such as those from Linksys or D-Link, which is communicatively coupled to remote system, e.g., through the Internet. Another implementation involves having a wireless network component in each system configured to communicate with a global wireless network, such as a cellular network, e.g., Verizon, or a Datacast network, e.g., from Ambient Devices.

Figure 4:
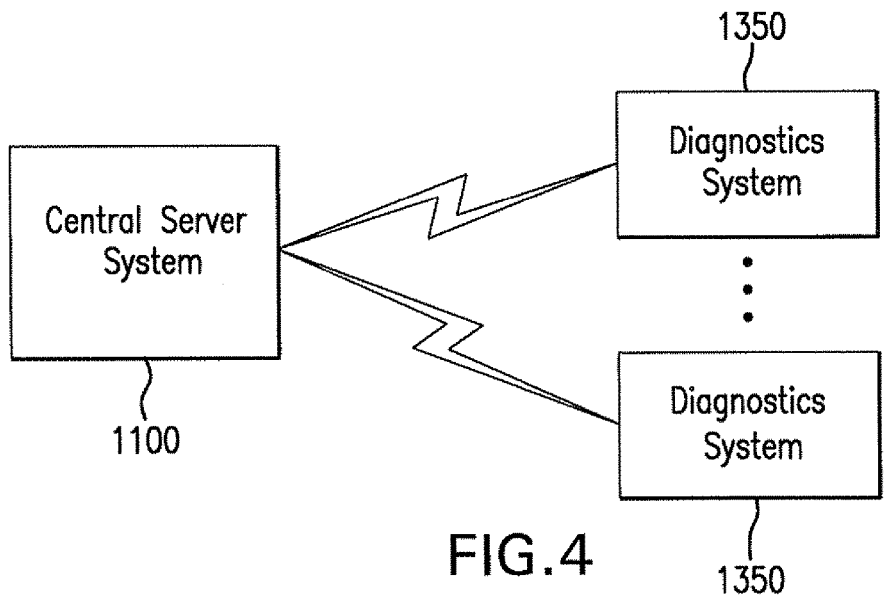
FIG. 4 is a diagram of a medical system in accordance with the teachings provided herein.

In addition to surgical profiles, the central server system 1100 can also be utilized to propagate diagnostics data for a particular patient to a particular surgical system 1300. Turning to FIG. 4, one or more diagnostics systems 1350 can be operatively in communication with the central server system 1100. The diagnostics systems 1350 can obtain relevant diagnostics data for a particular patient and upload the data to the central server system 1100. The data can be associated with a particular surgeon's profile in the profile directory 1160, which could include a directory of patients and their respective patient data. Such data can then be broadcasted/downloaded to the appropriate surgical system(s) 1300. This can be particularly useful in the case where the surgical system 1300 is a corneal correction system, such as an excimer laser system. The diagnostics system 1350 could be a wavefront aberrometer known in the art, such as COAS™ from Wavefront Sciences, Inc., that obtains wavefront measurements from a patient that is used by the corneal correction system for making the proper corneal corrections in a patient's eye.

The diagnostics system 1350 can include networking and/or wireless networking capabilities described above to upload the information to a central server system 1100 to be associated with the proper surgeon and/or surgical system 1300 and ultimately downloaded to the appropriate surgical system 1300. Patient and surgeon data can likewise be downloaded to the appropriate diagnostics system 1350 from the central server system 1100 which can be used to review and confirm accuracy of data and to also prompt for missing data.

Figure 5:
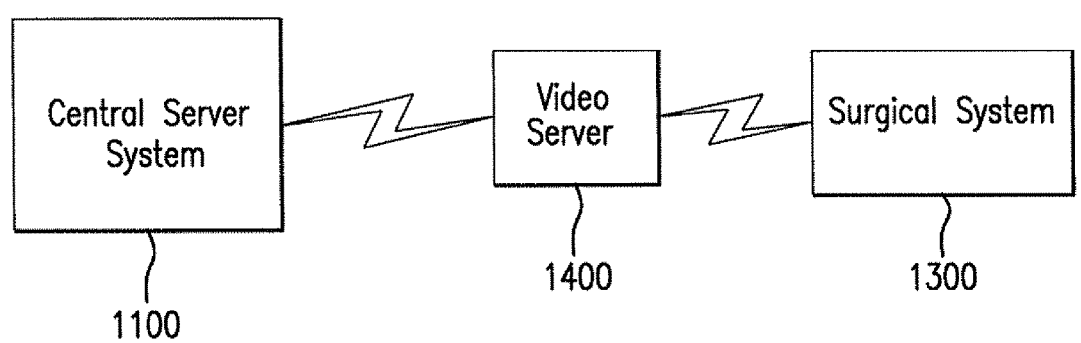
FIG. 5 illustrates data transmission via a video server.

FIG. 5 illustrates another embodiment of propagation or transmission of data from central server system 1100 to surgical system 1300 using a video server 1400. As implied by the devices shown in FIG. 5, the information to and from the surgical system 1300 and central server system 1100 may be carried over various devices or intermediate nodes, including but not limited to a video server 1400. Typical functionality of the video server 1400 is to provide video from the surgical system 1300 to the central server system 1100, such as video of a phacoemulsification procedure for archiving or analysis purposes. Video can also be provided from the central server system 1100 to surgical system 1300 via video server 1400, such as training videos or previously recorded videos of the patient undergoing a procedure.

Figure 6:
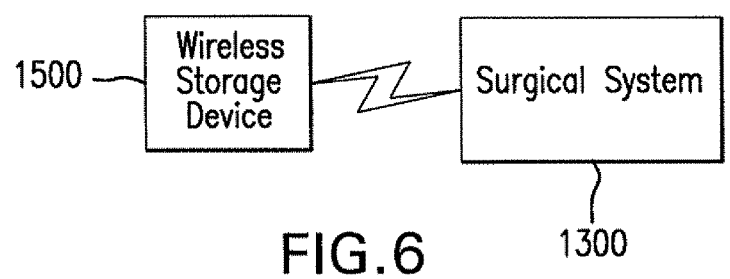
FIG. 6 shows a wireless transmission aspect of the current design.

FIG. 6 illustrates an alternative aspect of the design including the surgical system 1300 interfacing with wireless storage device 1500 for the purpose of storing information received wirelessly and/or to be transmitted wirelessly.

In operation, the surgeon may set up her profile from any internet enabled device via the internet, or alter her profile via the internet using a web browser or other software configured for this purpose. The surgeon then simply needs to identify herself to a surgical system 1300 such as a phacoemulsification or corneal correction machine, and the machine can obtain her desired surgical parameters from central server system 1100. Downloading of the profile may occur wirelessly, such as by wireless transmission from central system server 1100 to surgical system 1300. All surgeon parameters are stored in the central server system 1100. Using the email, chat, web pages, and other communicative functionality of central server system 1100, a surgeon can publish or broadcast his profile to other surgeons or users when desired by sending a request to the central server system 1100 and surgeon account database or directory 1160 via surgeon account or profile manager 1170 to do so. With appropriate authorization, other surgeons or users could download a profile or multiple profiles to client devices and/or surgical systems 1300. The surgeon can also identify patients to be operated on and thus have the surgeon's surgical system 1300 download and receive patient data and diagnostics information from a diagnostics system 1350 if available.

One alternate embodiment of the current design is the use of an authentication system, such as a badge reader and badge or keycard style system. Whenever an authorized user or surgeon having a key card or badge presents that key card or badge to an appropriate reader associated with a surgical system 1300, the surgeon may be afforded the opportunity to download his profile or parameters or appropriate patient data to the surgical system 1300, or such downloading may occur automatically when the individual presents the appropriate credentials. A password or other credential authentication scheme may be employed at the surgical system 1300 or at another appropriate location in the system.

A further aspect of the present system is the ability to provide usage statistics, maintenance parameters, and other pertinent information from a surgical system 1300 to central server system 1100. The surgical system 1300, such as a phacoemulsification machine, can wirelessly transmit data back to central server systems 1100 regarding the number of times or number amount of time the surgical system 1300 has been used, the number of disposable units used, such as phacoemusification packs, whether enough usage has occurred to require maintenance, and whether any detected problems exist. A system that provides usage statistics and maintenance parameters is described in U.S. Pat. No. 6,036,458, which is hereby incorporated by reference in its entirety.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A method for providing medical system operating parameters to surgical systems, the method implemented on a computing device and comprising:
   collecting, at the computing device, a medical practitioner's desired settings for operating a medical device within at least one medical system profile;
   enabling at least one authorized user to employ the computing device to alter said one medical system profile; and
   causing the computing device to transmit said one medical system profile and the medical practitioner's desired settings for operating the medical device to at least one surgical system pursuant to predetermined propagation parameters.

2. The method of claim 1, wherein said predetermined propagation parameters comprise a periodic propagation of at least one medical system profile to at least one surgical system.

3. The method of claim 1 wherein said predetermined propagation parameters comprise an operator initiated propagation of at least one medical system profile to at least one surgical system.

4. The method of claim 1, wherein said collecting comprises obtaining operating parameters from the authorized user employing at least one from a group comprising:
   a client device; and
   the surgical system.

5. The method of claim 4, wherein the client device comprises a personal computer.

6. The method of claim 1, further comprising establishing a medical profile in a medical profile directory prior to said enabling.

7. The method of claim 1, wherein said propagating at least partially occurs over a wireless network.

8. A medical system comprising:
   one or more surgical systems each having a plurality of surgeon desired medical device operational settings configurable by a surgeon;
   a central server communicatively accessible by the one or more surgical systems via a network, wherein the central server is configured to receive, store, and manage one or more surgeon profiles that each define the plurality of surgeon desired medical device operational settings for a particular surgeon to be downloaded to the one or more surgical systems.

9. The medical system of claim 8, further comprising one or more diagnostics systems communicatively accessible by the central server and configured to receive and upload patient diagnostics data to the central server to be downloaded to one of the one or more surgical systems.

10. The medical system of claim 9, wherein the patient diagnostics data is further associated with at least one of the one or more surgeon profiles.

11. The medical system of claim 8, wherein the communicative accessibility is wireless.

12. The medical system of claim 8, wherein the one or more surgeon profiles is viewable by any computing system in communication with the central server.

* * * * *